US00PP33776P2

(12) United States Plant Patent
Meyer

(10) Patent No.: US PP33,776 P2
(45) Date of Patent: Dec. 21, 2021

(54) ***SORGHASTRUM* PLANT NAMED 'MNYG318153'**

(50) Latin Name: *Sorghastrum nutans*
Varietal Denomination: MNYG318153

(71) Applicant: Regents of the University of Minnesota, Minneapolis, MN (US)

(72) Inventor: Mary Hockenberry Meyer, Plymouth, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 33 days.

(21) Appl. No.: 17/070,252

(22) Filed: Oct. 14, 2020

Related U.S. Application Data

(60) Provisional application No. 62/995,225, filed on Jan. 21, 2020.

(51) Int. Cl.
*A01H 5/12* (2018.01)
*A01H 6/46* (2018.01)

(52) U.S. Cl.
USPC ..... Plt./393
CPC ..... *A01H 6/466* (2018.05)

(58) Field of Classification Search
USPC ..... Plt./393
CPC ..... A01H 6/466
See application file for complete search history.

*Primary Examiner* — Anne Marie Grunberg
(74) *Attorney, Agent, or Firm* — Penny J. Aguirre

(57) ABSTRACT

A new cultivar of *Sorghastrum* plant named 'MNYG318153' that is characterized by its upright growth habit that does not lodge or fall over, its wide foliage that is olive green in color, its early blooming habit, and its large flowers that are yellow in color.

2 Drawing Sheets

Botanical classification: *Sorghastrum nutans*.
Varietal denomination: 'MNYG318153'.

BACKGROUND OF THE INVENTION

The present invention relates to a new and distinct cultivar of *Sorghastrum nutans* and will be referred to hereafter by its cultivar name, 'MNYG318153'. 'MNYG318153' represents a new cultivar of Indian grass, an ornamental grass grown for landscape use.

'MNYG318153' was discovered in 2005 by the Inventor as a chance seedling of *Sorghastrum nutans* in a trial field in Chaska, Minn.

Asexual propagation of the new cultivar was first accomplished by division in 2010 by the Inventor in Chaska, Minn. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'MNYG318153' as a unique cultivar of *Sorghastrum*.

1. 'MNYG318153' exhibits an upright growth habit that does not lodge or fall over.
2. 'MNYG318153' exhibits wide foliage that is olive green in color.
3. 'MNYG318153' exhibits an early blooming habit.
4. 'MNYG318153' exhibits large flowers that are yellow in color.
5. 'MNYG318153' exhibits cold hardiness at least to U.S.D.A. Zone 3.

'MNYG318153' can be most closely compared to *Sorghastrum nutans* cultivars 'Sioux Blue' (not patented) and 'Indian Steel' (not patented). 'Sioux Blue' is similar in plant height. 'Sioux Blue' differs from 'MNYG318153' in having foliage that is blue and blue-green in color, a later blooming season and in being derived from germplasm in Southern states. 'Indian Steel' is similar to 'MNYG318153' in plant height and in flower size. 'Indian Steel' differs from 'MNYG318153' in having foliage that is blue in color, a later blooming season and in being derived from germplasm in Southern states.

BRIEF DESCRIPTION OF THE DRAWINGS

The accompanying photographs were taken of 9-year-old plants as grown in a trial garden in Chaska, Minn. and illustrate the characteristics of the new cultivar.

The photograph in FIG. 1 provides a view of the plant habit of multiple plants of 'MNYG318153'.

Figure 1:
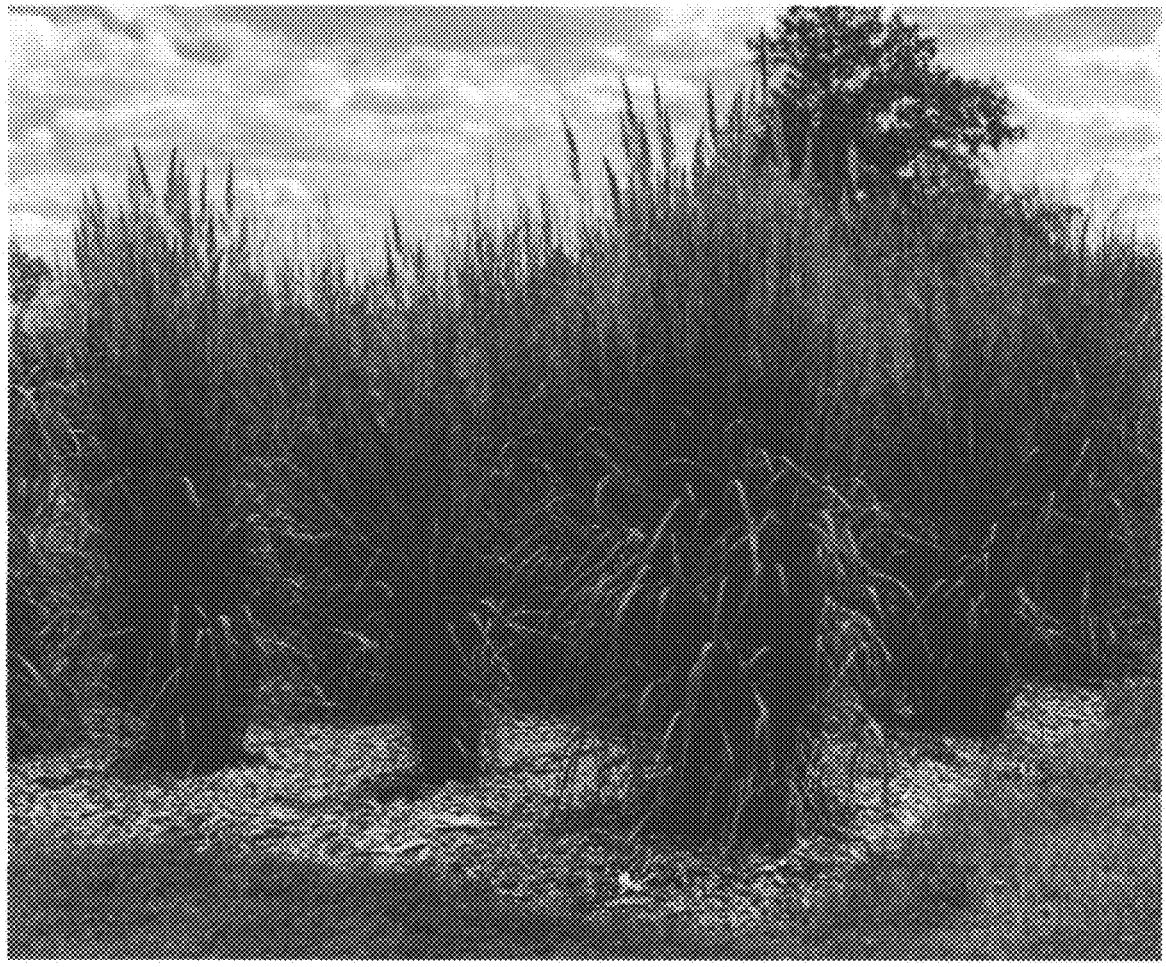
Figure 2:
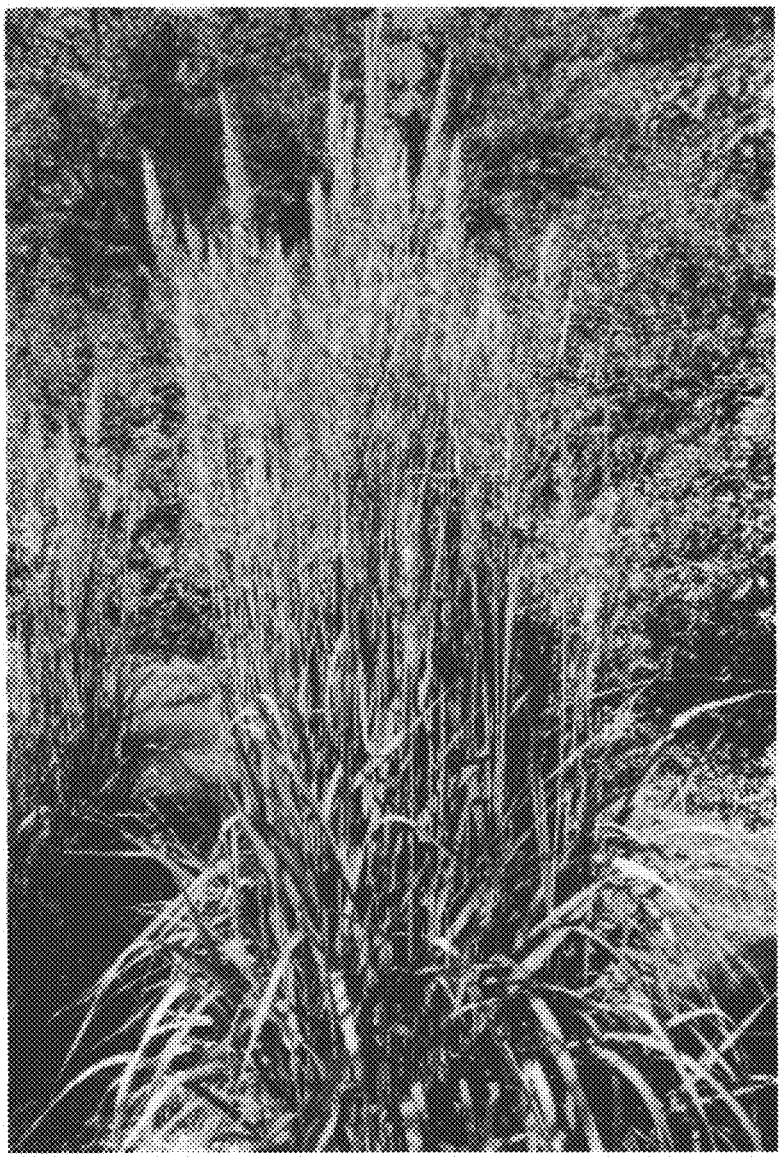

The photograph in FIG. 2 provides a view of the foliage and inflorescences of 'MNYG318153'.

The colors in the photographs are as close as possible with the digital photography techniques available, the color values cited in the detailed botanical description accurately describe the colors of the new *Sorghastrum*.

DETAILED BOTANICAL DESCRIPTION

The following is a detailed description of nine-year-old plants of the new cultivar as grown in a garden setting in Chaska, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—August 15 first anthesis (pollen shed) for approximately 3 weeks to September 10 with floral interest through winter in Chaska, Minn.

*Plant type*.—Herbaceous perennial grass.

*Plant habit*.—Upright growth habit that does not lodge or fall over.

*Height and spread*.—Up to 2 m in height and 91 cm in spread.

*Cold hardiness*.—U.S.D.A. Zone 3.

*Diseases*.—No resistance to susceptibility to diseases has been observed.

*Root description*.—Fibrous, fine, 161D in color.

*Propagation*.—Division and tissue culture.

*Growth rate*.—Vigorous to moderate.

Culm (stem) description:

*General*.—Rounded, solid pith at the nodes, strong, erect.

*Culm number*.—An average of 50 as grown in a 2-gallon container.

*Culm color*.—147C in summer, 145C and 162A in fall and 162B in winter.

*Culm size*.—Average of 3 mm in diameter, averaging 206 cm in height, 206 cm from the base to the tip of the flower panicle.

*Culm surface*.—Glabrous and slightly glossy.

*Internode length*.—An average of 17 cm between basal nodes, increasing to 22, and 30 and finally 40 between upper internodes.

Foliage description:

*Leaf shape*.—Narrowly lanceolate.

*Leaf division*.—Simple.

*Leaf margin*.—Entire.

*Leaf base*.—Sheathed to base of culm.

*Leaf apex*.—Sharply attenuate.

*Leaf venation*.—Parallel.

*Leaf width*.—Average of 17 cm at widest section.

*Leaf length*.—Overall average of 47 cm; basal leaves 56 cm, upper leaves 37 cm.

*Leaves per culm*.—Average of 4.4.

*Leaf surface*.—Glabrous and dull on both surfaces.

*Ligule*.—2 to 3 mm in length, stiff membranous, often deeply notched.

*Leaf color* (*both surfaces*).—Summer 147A; fall 163B and winter 164D.

Flower description:

*Inflorescence type*.—Narrow panicle of racemes at terminus of stem, primarily symmetrical.

*Inflorescence size*.—Panicle; an average of 23 cm in length and 4-6 cm in width during anthesis; after anthesis 2 cm in width; racemes an average of 8 cm in length and 4 cm in width.

*Spikelet description*.—Average of 300 per panicle, glumes; 4 mm in length and 3 mm in width, 164B in color, convex, lustrous surface, with soft hairs; lemmas 2, 3.5 mm in length and 1.5 mm in width, convex, glabrous surface, 164B; palea 1.5 mm in length, and 164B in color, convex, glabrous surface.

*Spikelet size*.—6-8 mm in length and 2 mm in width, awn 1-2.2 cm in length, once geniculated.

*Rachis*.—An average of 87 cm from last leaf and node, panicle portion an average of 23 cm in length, 4 to 7 cm wide at anthesis; 2 to 3 cm wide post anthesis; with branches an average of 6.5 cm in length and 1-2 cm in width, glabrous surface, 162A fall color, 162B in winter spikelet pedicel an average of 4 mm in length, wiry, 162A in color, glabrous surface, internode length of racemes ranges from 3 to 7 cm.

Reproductive organs:

*Androecium*.—Anthers; 3, 2.5 mm in length and 1 mm in width, 11A in color, longitudinal dehiscence, very fine filament 155B in color, pollen abundant at anthesis and 11A in color.

*Gynoecium*.—Pistil; 1, 2 plumose stigmas on short, fine styles about 0.3 mm in length and 145D in color, stigma; 84B in color, 1.5 mm in length and 1 mm in width, ovary; 1-locular, superior, elliptic in shape, 1 mm in length, 145D in color.

*Caryopsis*.—An average of 4 mm in length and about 1.5 in width, a blend of 165A and 165C in color.

It is claimed:

1. A new and distinct cultivar of *Sorghastrum* plant named 'MNYG318153' as herein illustrated and described.

* * * * *